United States Patent
Madsen et al.

(10) Patent No.: US 8,399,078 B2
(45) Date of Patent: Mar. 19, 2013

(54) FOIL

(75) Inventors: Nils Berg Madsen, Jyllinge (DK); John Stern Nielsen, Allerod (DK)

(73) Assignee: Novo Nordisk A/S, Bagsvaerd (DK)

( * ) Notice: Subject to any disclaimer, the term of this patent is extended or adjusted under 35 U.S.C. 154(b) by 733 days.

(21) Appl. No.: 11/283,653

(22) Filed: Nov. 21, 2005

(65) Prior Publication Data
US 2006/0134358 A1 Jun. 22, 2006

Related U.S. Application Data

(63) Continuation of application No. PCT/DK2004/000440, filed on Jun. 23, 2004.

(60) Provisional application No. 60/504,715, filed on Sep. 22, 2003, provisional application No. 60/523,349, filed on Nov. 19, 2003, provisional application No. 60/524,793, filed on Nov. 25, 2003, provisional application No. 60/525,469, filed on Nov. 26, 2003.

(51) Int. Cl.
B32B 27/32 (2006.01)
B32B 1/00 (2006.01)
A61B 19/00 (2006.01)

(52) U.S. Cl. ............ 428/35.7; 428/35.2; 604/408

(58) Field of Classification Search ........ 428/35.2, 428/35.7, 36.92; 62/60; 64/457.9; 206/438, 206/570, 828; 383/110, 113; 604/403, 408, 604/410
See application file for complete search history.

(56) References Cited

U.S. PATENT DOCUMENTS

| | | | |
|---|---|---|---|
| 3,087,491 A | 4/1963 | Geweck et al. | |
| 3,403,064 A | 9/1968 | Bellamy | |
| 4,212,299 A | 7/1980 | Yokokoji et al. | |
| 4,370,187 A | 1/1983 | Katagiri et al. | |
| 4,874,386 A | 10/1989 | O'Boyle | |
| 5,000,739 A | 3/1991 | Kulisz et al. | |
| 5,176,634 A * | 1/1993 | Smith et al. | 604/87 |
| 5,205,820 A | 4/1993 | Kriesel | |
| 5,366,839 A | 11/1994 | Aoki | |
| 5,722,957 A | 3/1998 | Steinbach | |
| 5,833,070 A | 11/1998 | Mizuno et al. | |
| 5,928,213 A | 7/1999 | Barney et al. | |
| 5,944,709 A | 8/1999 | Barney et al. | |
| 5,945,187 A * | 8/1999 | Buch-Rasmussen et al. | 428/36.92 |
| 6,010,485 A | 1/2000 | Buch-Rasmussen et al. | |
| 6,238,607 B1 | 5/2001 | Tsai et al. | |
| 6,287,652 B2 | 9/2001 | Speckhals et al. | |
| 6,306,503 B1 | 10/2001 | Tsai | |
| 6,312,776 B1 | 11/2001 | Finkelstein et al. | |
| 6,432,542 B1 | 8/2002 | Tsai | |
| 6,519,241 B1 | 2/2003 | Theimer | |

(Continued)

FOREIGN PATENT DOCUMENTS

| | | |
|---|---|---|
| CA | 2411202 | 11/2001 |
| CN | 1281687 | 1/2001 |

(Continued)

OTHER PUBLICATIONS

English Abstract for JP54-103184.

(Continued)

Primary Examiner — Erik Kashnikow
(74) Attorney, Agent, or Firm — Wesley A. Nicolas; Marc A. Began; Reza Green

(57) ABSTRACT

A container consisting of at least two layers, the inner layer consisting of a PE or PP film and the PCTFE layer consisting of a PCTFE film, and the thickness of the PCTFE layer being about 40-100 μm, which container is equipped with a device where the liquid can be lead out through when desired and which container is transparent, shows superior properties for storing liquid pharmaceutical compositions, especially insulin compositions containing preservatives.

18 Claims, 3 Drawing Sheets

U.S. PATENT DOCUMENTS

| | | |
|---|---|---|
| 6,572,542 B1 | 6/2003 | Houben et al. |
| 6,592,978 B1 | 7/2003 | Miller et al. |
| 6,713,165 B1 | 3/2004 | Karsten |
| 7,807,242 B2 | 10/2010 | Soerensen et al. |
| 7,838,109 B2 | 11/2010 | Declerck |
| 2001/0008694 A1 | 7/2001 | Tsai et al. |
| 2002/0007154 A1 | 1/2002 | Hansen et al. |
| 2002/0197478 A1 | 12/2002 | Muggli et al. |
| 2003/0008152 A1 | 1/2003 | Tsai et al. |
| 2003/0014014 A1 | 1/2003 | Nitzan |
| 2003/0047467 A1 | 3/2003 | Smith et al. |
| 2003/0203141 A1* | 10/2003 | Blum et al. .................. 428/35.7 |
| 2004/0001655 A1 | 1/2004 | Proicou et al. |
| 2004/0044332 A1 | 3/2004 | Stergiopulos |
| 2005/0113650 A1 | 5/2005 | Pacione et al. |
| 2005/0214129 A1 | 9/2005 | Greene et al. |
| 2005/0215867 A1 | 9/2005 | Grigsby et al. |
| 2006/0134358 A1 | 6/2006 | Madsen et al. |
| 2008/0176789 A1 | 7/2008 | Bang |

FOREIGN PATENT DOCUMENTS

| | | |
|---|---|---|
| DE | 19509632 | 3/1996 |
| DE | 19850607 | 5/2000 |
| DE | 203 06 931 U1 | 7/2003 |
| EP | 062341 | 10/1982 |
| EP | 0 132 583 B1 | 6/1984 |
| EP | 0 112 406 A1 | 7/1984 |
| EP | 898466 | 3/1999 |
| EP | 1 033 326 A1 | 3/2000 |
| EP | 1 013 193 A2 | 6/2000 |
| EP | 1258234 | 11/2002 |
| EP | 1 287 909 A2 | 3/2003 |
| EP | 1 364 638 A2 | 11/2003 |
| EP | 1525873 | 4/2005 |
| FR | 2850027 | 7/2004 |
| GB | 1591247 | 6/1981 |
| JP | 54-103184 | 8/1979 |
| JP | 63-224944 A | 9/1988 |
| JP | ll08-104369 | 4/1996 |
| JP | 2000-510728 | 8/2000 |
| JP | 2002-28999 | 1/2002 |
| RU | 2291681 | 1/2007 |
| WO | WO 90/01958 | 3/1990 |
| WO | WO 93/06158 | 4/1993 |
| WO | WO 93/06159 | 4/1993 |
| WO | 95/16565 | 12/1994 |
| WO | WO9742897 | 11/1997 |
| WO | 99/37269 | 1/1999 |
| WO | 00/61062 | 3/2000 |
| WO | 01/89607 | 5/2001 |
| WO | 02/40083 | 11/2001 |
| WO | WO 03/043494 | 5/2003 |
| WO | 03/091019 A1 | 11/2003 |
| WO | WO 03/099358 | 12/2003 |
| WO | WO03/099358 | 12/2003 |
| WO | WO 2004/098405 | 11/2004 |
| WO | WO 2005/000580 | 1/2005 |
| WO | WO 2005/037092 | 4/2005 |
| WO | WO 2005/087091 | 9/2005 |
| WO | WO 2007/077255 A2 | 7/2007 |
| WO | WO 2007/077255 A3 | 7/2007 |
| WO | WO 2008/058997 | 5/2008 |

OTHER PUBLICATIONS

English Abstract for DE 19850607.
English Abstract for DE 19509632.
English language abstract of FR 2850027.
Yinghong, Ou, The Publish of Enginery Industry, Plastics Handbook, 1991, pp. 364.
English Abstract of JP2002028999.
English Abstract of JPH08-104369.
Non-Final Office Action Mailed Oct. 12, 2010 in U.S. Appl. No. 11/917,202, filed Dec. 12, 2007; First named inventor: Sparholt.
Final Office Action Mailed Apr. 5, 2011 in U.S. Appl. No. 11/917,202, filed Dec. 12, 2007; First named inventor: Sparholt.
Search Report issued in connection with commonly owned European Application No. 05105731.3, mailed Nov. 18, 2005.
International Search Report and Written Opinion issued in connection with commonly owned International Application No. PCT/EP2006/063395, mailed Sep. 20, 2006.
International Preliminary Examination Report issued in connection with commonly owned PCT Application No. PCT/EP2006/063395, mailed Jan. 18, 2008.
International Search Report issued in commonly owned International Application No. PCT/EP2007/062341, dated Dec. 8, 2008.
English Abstract for JP54-103184, Aug. 1979.
English Abstract for DE 19850607, May 2000.
English Abstract for DE 19509632, Apr. 1971.
WAAC Newsletter, Burke, J., 1992, vol. 14, Part 2, pp. 13-17.
Final Rejection in U.S. Appl. No. 11/283,653, sent from the USPTO on Mar. 12, 2009.
Non-Final Office Action in U.S. Appl. No. 11/283,653 sent from the USPTO on Aug. 7, 2008.
English language abstract of FR 2850027, Jul. 2004.
Non-Final Office Action in U.S. Appl. No. 12/159,799 sent from USPTO on Sep. 23, 2009.
Yinghong, Ou, The Publish of Enginery Industry, Plastics Handbook, 1991, p. 364.
English Translation of Ou Yinghong et al., Handbook of Plastics, p. 364 (Feb. 1999).
Non-Final Office Action Mailed on Oct. 5, 2009 in U.S. Appl. No. 11/472,831, filed Jun. 22, 2006 by Soerensen et al.
Final Office Action Mailed on Mar. 11, 2010 in U.S. Appl. No. 12/159,799, filed Jul. 1, 2008 by Glejboel et al.
English Abstract of JP2002028999, Jan. 2002.
English Abstract of JPH08-104369, Apr. 1996.
Derwent abstract of JP 63-224944 A, Sep. 1988. cited by examiner.

* cited by examiner

Cross section through the wall of a container of this invention

FOIL

CROSS REFERENCE TO RELATED APPLICATIONS

This application is a continuation of international application Ser. No. PCT/DK2004/000440 filed Jun. 23, 2004 which claims priority of Danish application nos. PA 2003 00971 filed Jun. 27, 2003; PA 2003 01717 filed Nov. 19, 2003; PA 2003 01741 filed Nov. 25, 2003; PA 2003 01746 filed Nov. 26, 2003 and U.S. provisional application Nos. 60/504,715 filed Sep. 22, 2003, 60/523,349 filed Nov. 19, 2003; 60/524,793 filed Nov. 25, 2003 and 60/525,469 filed Nov. 26, 2003, all of which are incorporated by reference.

FIELD OF THIS INVENTION

The present invention relates to a transparent plastic container which can be used to storage of liquid solutions or suspensions, for example of medicaments, optionally containing preservatives.

BACKGROUND OF THIS INVENTION

Some medicaments are delivered to the patients in solid form, other in liquid form. Often, the liquid medicaments are delivered in a container. Some container consists only or mainly of glass, other consists only or mainly of other materials such as plastic.

Medicaments in solid form are often marketed in a glass container or a plastic container. An example of a plastic container is a blister package.

In a pharmaceutical composition in liquid form, the active ingredient is present in dissolved or suspended form. In addition to the active ingredient, a pharmaceutical composition may contain a pharmaceutically active carrier, a disintegrater, a stabalizer, or a buffer substance.

The route of administration varies between the different medicaments. Some medicaments are administered via the oral route, other are administered by injecting the medicament to the patient, for example, intravenously or subcutaneously. Many medicaments being peptides, for example, insulin, are administered by injections. Earlier, syringes were used for the injections. As far as insulin is concerned, it is becoming more and more common to use so called pen systems for the injections. Furthermore, the use of pumps for administration by injection may become a popular way of administrations by injections. In some of the pumps, the aqueous composition will be present in a glass reservoir or another hard reservoir, in other pumps, aqueous compositions will be present in a flexible reservoir, for example a reservoir which is wholly or mainly made of another material than glass, for example of plastic.

For many aqueous compositions, it is extremely difficult to find a non-glass material which can safely be used to store said aqueous composition until it is used by the patient. One of the many difficulties is the high mobility of preservatives in welding layer based on polymers like polyethylene (herein designated PE), polypropylene (herein designated PP), polyethylene terephtalate (herein designated PET) or the like combined with a high affinity of the preservatives to the widely used adhesives based on polyurethane used for lamination of welding layer to a moist barrier like polychlorotrifluoroethylene (herein designated PCTFE). The result of tests of the known art plastic products containing a solution of a medicament with preservatives is that a fast and not desired reduction in the content of preservative in the medicated solution takes place. A main task for the inventors of this invention has been to find a material or combination of materials which can be used to prepare a transparent, flexible container fulfilling the safety requirements for storage of pharmaceutical solutions containing a preservative such as phenol, m-cresol and benzyl alcohol. It was extremely difficult to find a material fulfilling these requirements.

Briefly, the object of this invention is to overcome or ameliorate at least some of the disadvantages of the prior art. Hence, not all the objects mentioned below may be fully overcome or ameliorated.

A more specific object of this invention is to furnish a container or reservoir.

Another object of this invention is to furnish a flexible container.

Another object of this invention is to furnish a transparent container.

Another object of this invention is to furnish a part allowing sterilization.

Another object of this invention is to furnish materials which may be welded to itself to form the above mentioned reservoir.

Another object of this invention is to furnish a container which can be used for storage of liquid solutions or suspensions of medicaments, optionally containing preservatives.

Another object of this invention is to furnish a container which has a sufficient transparency so as to enable inspection of the content of the container.

Another object of this invention is to furnish a container which can be used to storage of liquid solutions or suspensions of medicaments, optionally containing preservatives and which container not or only to a minor degree consists of glass.

Another object of this invention is to furnish a container having barrier properties securing that the concentration of the active ingredient in the aqueous composition is not changed substantially during storage for a sufficient period of time.

Another object of this invention is to furnish a container having barrier properties securing that the concentration of any preservative present in the aqueous composition is not changed substantially during storage for a sufficient period of time.

Another object of this invention is to furnish a container which can be welded tightly against a suitable septum material.

Another object of this invention is to furnish a container which can be adhered tightly against a suitable septum material by other means than welding.

A further object of this invention is to furnish a film for a pouch which can be used for storage of sterile water based drug formulation.

A further object of this invention is to furnish a pouch which can be used as reservoir for a pump and, preferably, said reservoir contains a water based drug formulation.

A further object of this invention is to furnish a film material for said pouch fulfilling certain functional requirements such as physical properties for the material after sterilization, chemical requirements for the material after sterilization, and cleanliness.

Hence, one object of this invention is to furnish a film material for said pouch which can be sterilized, for example, using gamma irradiation, electron beam, steam, or ethylene oxide.

A further object of this invention is to furnish a film material for said pouch which, after sterilization, fulfills most of or all the following physical requirements: 1) the material must be transparent, 2) the material must provide a good barrier against water; 3) the material must provide a good barrier against gasses (for example, oxygen and carbon dioxide); 4) the material must provide a good barrier against preservatives (for example, phenol and meta-cresol); 5) the material must provide a good barrier against odors (for example preservatives); 6) the material must be resistant against environmental stress cracking (for example, oils, perfumes); 7) the material must be resistant against flex-crack; 8) the material must have good sealing properties (for example, by welding); 9) the material must not delaminate after sterilization, during processing or storage; and 10) the material must not relax significantly during storage and use.

A further object of this invention is to furnish a film material for said pouch which, after sterilization, fulfills most of or all the following chemical requirements: 1) the material must not emit substances to the drug which can affect the health and safety of the patient (leachables); 2) the material must have a very low level of extractables; and 3) the material must be compatible with the drug formulation.

A further object of this invention is to furnish a film material for said pouch which, after sterilization, fulfills the following requirements for cleanliness: 1) it shall be possible to prepare the material under hygienic conditions; and 2) the final product must be free of dust and particles.

A further object of this invention is to furnish a film for said pouch fulfilling certain health and safety requirements, preferably most of or all the requirements mentioned in 1) European Pharmacopoeia (Ph. Eur.) 2002, $4^{th}$ edition; 2) The United States Pharmacopeia (USP) 25; 3) Japanese Pharmacopeia (JP) XIV; 4) EEC Directive 90/128+amendments "Relating to plastics materials and articles intended to come into contact with foodstuffs"; 5) Code of federal regulations (CFR) Title 21 Food and Drugs, part 170-190; 6) III /9090/90 EN. Plastic Primary Packaging Materials. Note for Guidance; and 7) Guidance for Industry. Container Closure Systems for Packaging Human Drugs and Biologics, Chemistry, Manufacturing, and Controls Documentation. FDA, May 1999.

DEFINITIONS

Co-extrusion covers a process where two or more polymer materials are melded in two or more extruders and co-extruded together through a flat nozzle or systems of flat nozzles and cooled to form the co-extruded foil.

Extrusion-lamination (also designated coex lamination) covers a process where a feedstock in form of a foil of one material is coated through a flat nozzle or systems of flat nozzles from one or more extruders with one layer or more layers of melted material or materials and then cooled to form the extrusion-lamination foil.

Lamination covers a process, where two feed stocks of foil materials are joined together by adding a proper adhesive to one foil, followed by addition of the second foil forming the laminated foil.

A tie layer is a layer which is placed between two polymer layers with the object of securing that the two layers are joined together.

The term container which herein also is designated pouch or reservoir is an item which may contain a liquid. This container is made of a foil or film.

The inner layer of the chamber of said container is in intimate contact with the liquid which is to be stored in said container.

Herein the term outer layer of the chamber of said container is a layer which is not in intimate contact with the liquid which is to be stored in said container. In other words, the inner layer is placed between the outer layer and said liquid. In relation to the layers, the terms inner and outer relates to the position of the two layers in relation to each other, the position of the liquid giving the direction of inner and outer. For example, this terminology does not preclude that a further layer can be adhered to the outer layer, at the outside thereof, the result of which being that, in fact, the so-called outer layer is placed between, on one hand, the so-called inner layer and, on the other hand, the additional layer adhered to the so-called outer layer, at the outside thereof.

A flexible item is an item that can bend or be bend easily and which does not break (unless it is bend too much). Glass is not flexible. Herein the term flexible in connection with the containers indicates that if the container is subjected to a force, for example, by being filled with a liquid, it will change its form without breaking.

Herein the term "insulin" refers to insulin from any species such as porcine insulin, bovine insulin, and human insulin and salts thereof such as zinc salts, and protamin salts as well as active derivatives of insulin, and insulin analogues. The term "active derivatives of insulin", is what a skilled art worker generally considers derivatives, vide general textbooks, for example, insulin having a substituent not present in the parent insulin molecule. The term "insulin analogues" refers to insulin wherein one or more of the amino acid residues have been exchanged with another amino acid residue and/or from which one or more amino acid residue has been deleted and/or from which one or more amino acid residue has been added with the proviso that said insulin analogue has a sufficient insulin activity. Using results from the so-called free fat cell assay, any skilled art worker, for example, a physician, knows when and which dosages to administer of the insulin analogue. Examples of insulin analogues are described in the following patents and equivalents thereto: U.S. Pat. No. 5,618,913, EP 254,516, EP 280,534, U.S. Pat. Nos. 5,750, 497, and 6,011,007. Examples of specific insulin analogues are insulin aspart (i.e., $Asp^{B28}$ human insulin), insulin lispro (i.e., $Lys^{B28}$,$Pro^{B29}$ human insulin), and insulin glargin (i.e., $Gly^{A21}$,$Arg^{B31}$,$Arg^{B32}$ human insulin). Herein, the term insulin also covers compounds which can be considered being both an insulin derivative and an insulin analogue. Examples of such compounds are described in the following patents and equivalents thereto: U.S. Pat. Nos. 5,750,497, and 6,011,007. An example of a specific insulin analogue and derivative is insulin detemir (i.e., des-$Thr^{B30}$ human insulin γ $Lys^{B29}$ tetradecanoyl).

The term "U", when used herein, refers to insulin units. Most of the currently used (marketed) insulins (bovine, porcine, human, lispro, aspart, and glargine) have a potency of one unit which equals 6 nmol. Long-acting acylated insulins have reduced potency compared to human insulin. Thus, for insulin detemir one unit corresponds to 24 nmol. For other insulins, the relation between U and nmol can be determined, if not known already, for example, by determining the amount giving a similar pharmacological (blood glucose lowering) effect as that of human insulin.

SUMMARY OF THE INVENTION

Briefly, this invention relates to a flexible, transparent, water-tight chamber comprised of a film comprising two layers, an inner layer and an outer layer, wherein the two layers are joined together to form the film and wherein the film is formed into a transparent pouch and wherein the pouch is sufficiently moisture proof, phenol proof and m-cresol proof to allow for extended storage of a medicament solution or suspension containing or consisting of water, phenol and/or m-cresol without significant changes in concentration of water, phenol, and m-cresol occurring over the extended time period and wherein the pouch is radiation sterilisable.

In another aspect, this invention relates to a method for storing a liquid solution and/or suspension of insulin for a significant period of time for use in a delivery device, the method comprising the steps of forming a pouch from a transparent polymer film, the film being sufficiently water resistant, phenol resistant, and m-cresol resistant to allow the insulin to age for two years without degradation of its pharmaceutical properties; sterilizing the pouch; and inserting the insulin compound into the pouch for storage for a significant period of time.

BRIEF DESCRIPTION OF THE DRAWINGS

FIG. 1 shows a cross section through the wall of the chamber in the container of this invention. The inner layer 2 is in intimate contact with the liquid which is to be stored in said container. Usually, the outer layer 1 (which may be a PCTFE layer) is not in contact with the liquid in the container. In this embodiment of this invention shown in FIG. 1, the inner and outer layers (PCTFE) are joined together using a tie layer 3.

FIG. 2 is identical with FIG. 1 with the proviso that in FIG. 2, the digits in FIG. 1 are exchanged by a proper, explanatory text.

DESCRIPTION OF THE PREFERRED EMBODIMENTS

Figure 1:
FIGS. 1 & 2 are examples of embodiments of this invention.
Figure 2:
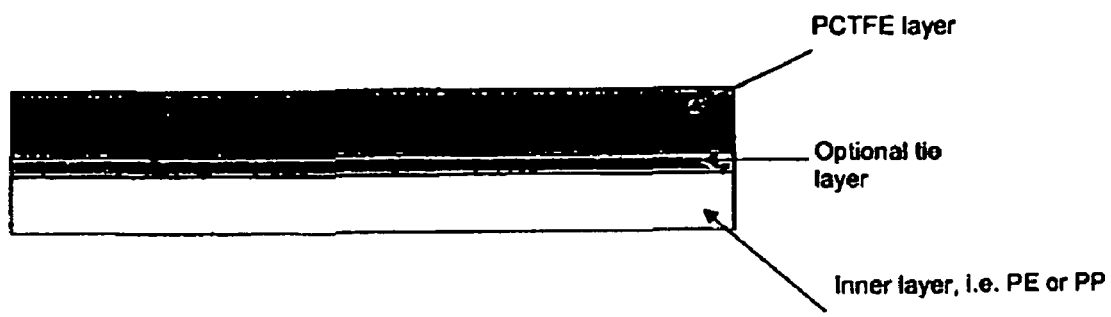
Figure 3:
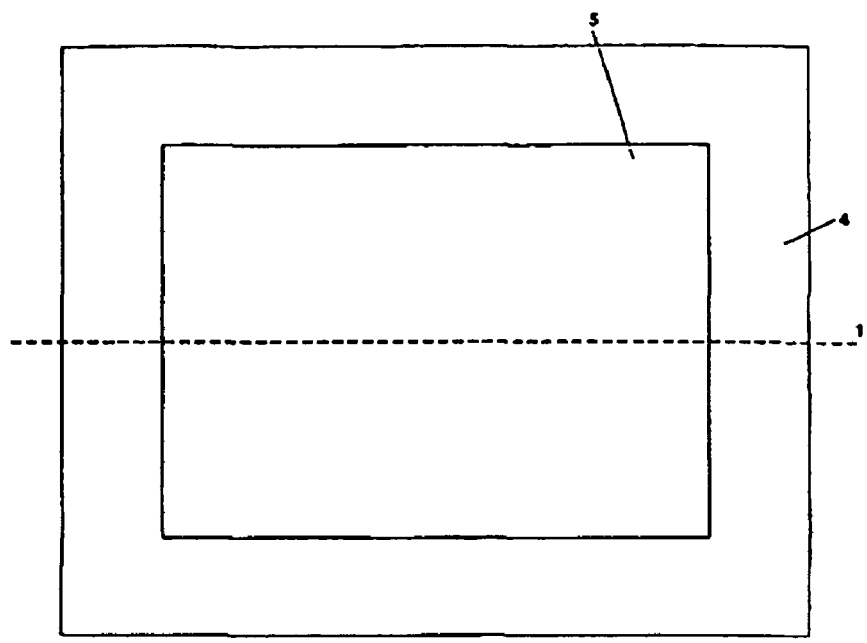
FIG. 3 shows one side of the flexible container. In this figure, the welding layer 4 secures that the container is tight. The inner of the container 5 may be filled with a liquid.
Figure 4:
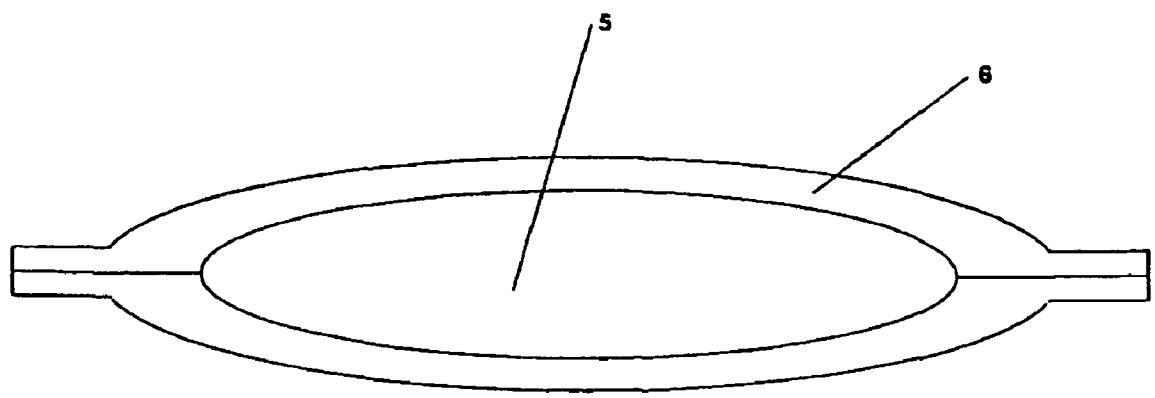
FIG. 4 is a view taken at the line 1-1 in FIG. 3 perpendicular to the surface shown in FIG. 3. The wall of the container 6 consists of the outer layer 1, the inner layer 2, and the tie layer 3.

Surprisingly, it has been found that a container described in the claims below fulfills the requirements set to a container which is to be used for storage of an aqueous solution, especially a solution of a medicament containing preservatives such as phenol or m-cresol.

In one aspect, this invention relates to a flexible, at least partially transparent container for storage of a liquid in a water-tight chamber, the wall material of which chamber comprises at least two layers, the inner layer of which is in intimate contact with said liquid when said chamber contains a liquid, and the outer layer which is not, or only to a minor or inferior degree, in contact with said liquid when said chamber contains a liquid, said inner and outer layers being joined intimately together, characterized in that when said chamber is filled with water and when it is stored at a temperature of about 5° C. for 24 months less than 10% (weight/weight) of the content of water diffuses out from the container; and when said chamber is filled with water containing about 1.8 mg/mL (19 mM) of phenol and when it is stored at a temperature of about 5° C. for 24 months, the change in the concentration of phenol in the liquid is less than about 10%.

In another aspect, this invention relates to a flexible, at least partially transparent container for storage of a liquid in a water-tight chamber, the wall material of which chamber comprises at least two layers, the inner layer of which is in intimate contact with said liquid when said chamber contains a liquid, and the outer layer which is not, or only to a minor or inferior degree, in contact with said liquid when said chamber contains a liquid, said inner and outer layers being joined intimately together, characterized in that when said chamber is filled with water and when it is stored at a temperature of about 5° C. for 24 months less than 10% (weight/weight) of the content of water diffuses out from the container; and when said chamber is filled with water containing about 1.8 mg/mL (19 mM) of phenol and when it is stored at a temperature of about 37° C. for 12 weeks, the change in the concentration of phenol in the liquid is less than about 10%.

According to a preferred embodiment of this invention, it relates to a container as described above, wherein the outer layer alone fulfills the requirement that when said chamber is filled with water and when it is stored at a temperature of about 5° C. for 24 months less than 10% (weight/weight), preferably less than 5% (weight/weight), even more preferred less than 3% (weight/weight) of the content of water diffuses out from the container.

According to another preferred embodiment of this invention, it relates to a container as described above, wherein the inner layer alone fulfills the requirement that when said chamber is filled with water containing about 1.8 mg/mL (19 mM) of phenol and when it is stored at a temperature of about 5° C. for 24 months, the change in the concentration of phenol in the liquid is less than about 10% ; or when said chamber is filled with water containing about 1.8 mg/mL (19 mM) of phenol and when it is stored at a temperature of about 37° C. for 12 weeks, the change in the concentration of phenol in the liquid is less than about 10%.

According to another preferred embodiment of this invention, it relates to a container as described above, wherein the inner layer is weldable.

According to another preferred embodiment of this invention, it relates to a container as described above, wherein the thickness of the inner layer is above about 10 μm, preferably above about 20 μm, and below about 60 μm, preferably below about 50 μm, even more preferred below about 40 μm.

According to another preferred embodiment of this invention, it relates to a container as described above, which when filled with water and when stored at a temperature of about 5° C. for 24 months less than 10% , preferably less than 5%, more preferred less than 2%, (weight/weight) of the content of water diffuses out from the container.

According to another preferred embodiment of this invention, it relates to a container as described above, from which when filled with water containing about about 1.8 mg/mL (19 mM) of phenol and when stored at a temperature of about 5° C. for 24 months, the change in the concentration of phenol is less than about 10% preferably less than about 5%, more preferred less than about 2%.

According to another preferred embodiment of this invention, it relates to a container as described above, from which when filled with water containing about 1.8 mg/mL (19 mM) of phenol and when stored at a temperature of about 37° C. for 12 weeks, the change in the concentration of phenol is less than about 10% , preferably less than about 5%, more preferred less than about 2%.

According to another preferred embodiment of this invention, it relates to a container as described above, from which when filled with water containing 2.06 mg/mL (19 mM) of m-cresol and when stored at a temperature of about 5° C. for 24 months, the change in the concentration of m-cresol is less than about 10% , preferably less than about 5%, more preferred less than about 2%.

According to another preferred embodiment of this invention, it relates to a container as described above, from which when filled with water containing 2.06 mg/mL (19 mM) of m-cresol and when stored at a temperature of about 37° C. for 12 weeks, the change in the concentration of m-cresol is less than about 10%, preferably less than about 5%, more preferred less than about 2%.

According to another preferred embodiment of this invention, it relates to a container as described above, which is prepared from a pouch foil which when tested by test A described below gives a maximum loss of m-cresol of about 10%, preferably not more than about 5%.

According to another preferred embodiment of this invention, it relates to a container as described above, which is prepared from a pouch foil which when tested by test A described below gives a change in the pH value which is than about +/−0.2.

According to another preferred embodiment of this invention, it relates to a container as described above, which is prepared from a pouch foil which when tested by the test B described below gives a maximum weight loss of about 2.5%, preferably not more than about 1%.

According to another preferred embodiment of this invention, it relates to a container as described above, which is prepared from a pouch foil which when tested by test B described below gives a maximum loss of m-cresol of about 10%, preferably not more than about 5%.

According to another preferred embodiment of this invention, it relates to a container as described above, which is prepared from a pouch foil which when tested by test B described below gives a change in the pH value which is more than about +/−0.2.

According to another preferred embodiment of this invention, it relates to a container as described above, which is prepared from a pouch foil which when tested by test C described below gives a maximum weight loss of 2.5%, preferably not more than about 2%.

According to another preferred embodiment of this invention, it relates to a container as described above, which is prepared from a pouch foil which when tested by test C described below gives a maximum loss of m-cresol of about 10%, preferably not more than about 5%.

According to another preferred embodiment of this invention, it relates to a container as described above, which is prepared from a pouch foil which when tested by test C described below gives a maximum loss of phenol of about 10%, preferably not more than about 5%.

According to another preferred embodiment of this invention, it relates to a container as described above, which is prepared from a pouch foil which when tested by test C described below gives a change in the pH value which is not more than about +/−0.2.

According to another preferred embodiment of this invention, it relates to a container as described above, which is prepared from a pouch foil which fulfills test D described below for the dilution 1:50, preferably the dilution 1:100, more preferred the dilution 1:200, even more preferred the dilution 1:400.

According to another preferred embodiment of this invention, it relates to a container as described above, which is flexible.

According to another preferred embodiment of this invention, it relates to a container as described above, which is equipped with a device whereby said liquid can be expelled from said container.

According to another preferred embodiment of this invention, it relates to a container as described above, wherein a third polymeric layer is added on the outer side of the PCTFE layer.

According to another preferred embodiment of this invention, it relates to a container as described above, which, when completely filled with liquid, can contain an amount of liquid which is at least about 0.5 ml, preferably at least about 1 ml, and not more than about 10 ml, preferably not more than about 5 ml, more preferred not more than about 2 ml and, preferably the volume is about 1.5 ml. According to a specific preferred embodiment of this invention, it relates to a container containing from about 2 ml to about 4 ml, preferably about 3 ml.

According to another preferred embodiment of this invention, it relates to a container as described above, which is filled partially or wholly with a liquid pharmaceutical composition.

According to another preferred embodiment of this invention, it relates to a container as described above, wherein at least 95% (volume/volume), preferably at least 98% (volume/volume), more preferred at least 99% (volume/volume), and even more preferred at least 99.9% (volume/volume), of the inner of the container contains the liquid pharmaceutical composition According to another preferred embodiment of this invention, it relates to a container as described above, which is filled partially or wholly with a liquid pharmaceutical composition wherein the active ingredient is a peptide.

According to another preferred embodiment of this invention, it relates to a container as described above, which is filled partially or wholly with a liquid pharmaceutical composition wherein the active ingredient is insulin.

According to another preferred embodiment of this invention, it relates to a container as described above, wherein the content of insulin in said container is in the range from about 10 U/ml to about 1500 U/ml.

According to another preferred embodiment of this invention, it relates to a container as described above, containing a solution or suspension containing a preservative.

According to another preferred embodiment of this invention, it relates to a container as described above, which is filled partially or wholly with a liquid pharmaceutical composition containing phenol.

According to another preferred embodiment of this invention, it relates to a container as described above, which is filled partially or wholly with a liquid pharmaceutical composition containing m-cresol.

According to another preferred embodiment of this invention, it relates to a container as described above, which is filled partially or wholly with a liquid pharmaceutical composition containing benzyl alcohol.

In another aspect, this invention relates to the use of a container as described above for storing a liquid pharmaceutical composition as mentioned above.

In just another aspect, this invention relates to a container for storage of a liquid in a water-tight chamber, the wall material of which chamber comprises at least two layers, the inner layer of which is in intimate contact with said liquid when said chamber contains a liquid, and another layer consisting of a PCTFE film which is not, or only to a minor or inferior degree, in contact with said liquid when said chamber contains a liquid, said inner layer consisting of a PE or PP film, and either said inner layer and said PCTFE layer being a coextrudate or an extrusion-laminate or said inner layer and said PCTFE layer being joined together, and the thickness of said PCTFE layer being above about 40 μm, and being below about 100 μm, preferably below about 75 μm.

According to a preferred embodiment of this invention, it relates to a container as described above, which is at least partially transparent.

According to a preferred embodiment of this invention, it relates to a container as described above, which is wholly transparent.

The inner layer of the container of this invention may consist of polyethylene (herein designated PE) or polypropylene (herein designated PE) or mixtures of PE and PP. PE consists of at least 75%, preferably at least 90%, more preferred at least 95%, (weight/weight) of polyethylene. PP consists of at least 75%, preferably at least 90%, more preferred at least 95%, (weight/weight) of polypropylene.

In a preferred embodiment of this invention, PE is as defined in European Pharmacopoeia 2001, $4^{th}$ Edition, point 3.1.5, the content of which is hereby incorporated by reference. Examples of components present in PE are higher alkene homologues ($C_3$ to $C_{10}$) and other additives mentioned therein.

In a preferred embodiment of this invention, PP is as defined in European Pharmacopoeia 2001, $4^{th}$ Edition, point 3.1.6, the content of which is hereby incorporated by reference. Briefly, PP consists of the homopolymer of propylene or of a copolymer of propylene with not more than 25% of ethylene or a mixture (alloy) of polypropylene with not more than 25% of polyethylene. It may contain additives, vide the above point 3.1.6.

In a preferred embodiment of this invention, the inner layer is a PCTFE layer consisting of at least 75%, preferably at least 90%, more preferred at least 95%, (weight/weight) of a polychlorotrifluoroethylene film, for example Aclar® from Honeywell, Morris Town, N.J., USA.

In another preferred embodiment of this invention, the outer layer is a PCTFE layer consisting of at least 75%, preferably at least 90%, more preferred at least 95%, (weight/weight) of a polychlorotrifluoroethylene film, for example Aclar® from Honeywell, Morris Town, N.J., USA.

The tie layer which may be used to secure that the inner and outer layers, e.g. the PCTFE layer, are joined together may consist of an adhesive, for example polyethyleneimine (hereinafter designated PEI) or any other suitable tie layer. Alternatively, the tie layer can be a polyolefin having at least one functional moiety of an unsaturated carboxylic acid or an anhydride thereof. Alternatively, the tie layer can be a polyolefin having at least one functional moiety of an unsaturated carboxylic acid or an anhydride thereof. Examples are: Lotader, Lotryl, Evatane and Orevac ex. ATOFINA, Lavamelt ex. BAYER, PROVISTA and EASTAR ex. EASTMAN, Bynel ex. DuPont, AMPLIFY and INTEGRAL ex. Dow.

Further examples of tie layers are mentioned in WO 98/25762, the content of which is hereby incorporated by reference. As an example of a specific tie layer, reference could also be made to that used in Aclar® Cx 130 from Honeywell.

It is important to elect a tie layer which does not have any undesired influence on the final material. In a preferred embodiment of this invention, the tie layer is so that only an inferior amount of phenol, m-cresol, or benzyl alcohol disappears during a period of 24 months at a temperature of 5° C. or a period of 12 weeks at 27° C. months, when an aqueous solution containing about 1.8 mg/ml of phenol is placed in a container according to this invention, vide the tests described below.

Known tie layers have a thickness of, for example 2 or 8 μm. According to a preferred embodiment of this invention, it relates to a container as described above, wherein the tie layer or tie layers in the foil has a thickness in the range from about 1 μm to about 10 μm, preferably below about 8 μm, more preferred below about 6 μm.

For the preparation of the containers according to this invention, the use of coex-laminated products is not limited to some of the specific polymer layers mentioned above such as PP or PE and PCTFE.

An example of a coex-laminated product not made of PP or PE and PCTFE is a coextrudated PE-PET foil laminated to PCTFE which can be prepared by use of standard lamination techniques known in the art. This structure has a remarkable barrier against mobile molecules like m-cresol.

Figure 5:
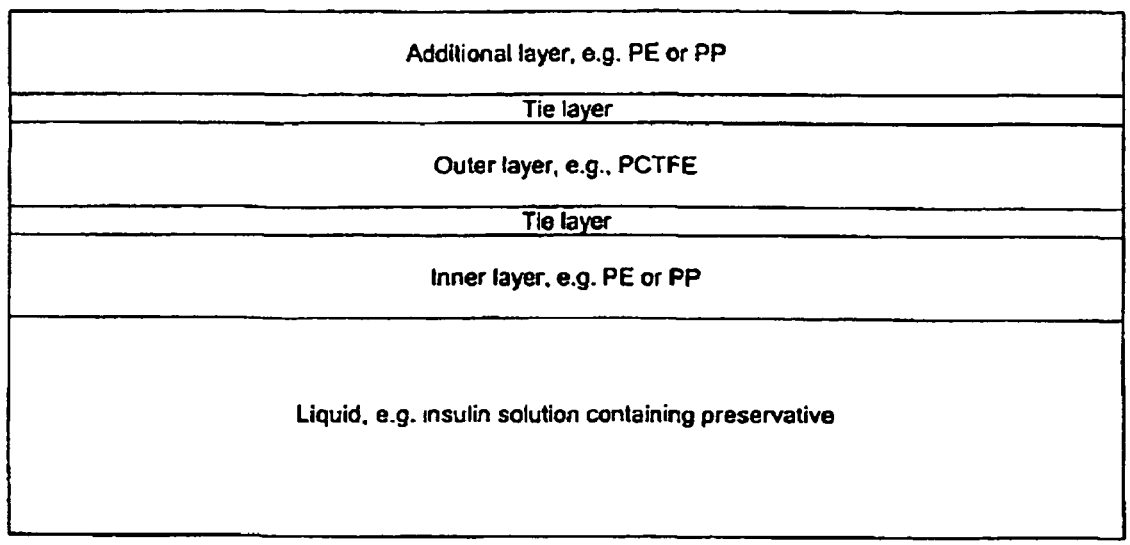
FIG. 5 shows a cross section through the wall of the chamber in a specific embodiment of this invention and a part of the adjacent liquid.

A third polymeric layer may be added on the outer side of the outer layer, e.g., on the outer side of the PCTFE layer. Examples of such a third layer are PP, PE, PET-G (polyethylene pthereptate glycerol modified), and TPE (thermoplastic elastomer), allowing welding from the outside of the reservoir. FIG. 5 shows an example where such a third polymeric layer is used. In this example, the additional layer may be the same or different from the inner layer. In a preferred embodiment of this invention, the additional layer and the inner layer are identical or almost identical.

In a preferred embodiment of this invention, the thickness of the inner layer is at least about 20 μm, preferably at least about 30 μm, and the thickness of the inner layer is not more than about 100 μm, preferably not more than about 75 μm.

A foil useful to produce a container of this invention consisting of a coextrudate may be prepared as follows:

A feedstock of PCTFE (pellets or powder), a feedstock of tie-layer, and a feedstock of PE are melted in three separated extruders and co-extruded in the molten state through flat nozzles in the preferred thickness and cooled and, thereafter, the foil is formed.

A foil useful to produce a container of this invention consisting of an extrudate-laminate may be prepared as follows:

A feedstock of PCTFE foil in the preferred thickness is converted by an extrusion-lamination process, where a melded tie layer is added to the PCTFE foil to function as a compatibilizer, followed by addition of a melded welding layer, e.g. PE, PP or any other polymer. The extrudate-laminate is cooled on a cooling drum or the like and winded. The chemical nature of the tie layer is so that it has a low affinity to aromatic preservatives like m-cresol and phenol.

A foil useful to produce a container of this invention consisting of a lamination may be prepared as follows:

Another useful method to produce a laminate is to use a feedstock of PCTFE foil in the preferred thickness in combination with an adhesive followed by an adhesive lamination with a foil of the preferred welding layer, e.g., the coextruded PET-PE, in the preferred thickness. The adhesive is typically based on polyurethane having a high affinity to aromatic preservatives like m-cresol and phenol.

A container of this invention wherein the two layers are joined together using a welding layer may be prepared as follows:

The welding layers are oriented against each other, and welded together by using any proper welding technique known in the art, for example, by heat, ultrasound, laser or the like.

The outer and inner periphery of the welding zone are determined taken into account the size and form of the reservoir.

The container according to this invention must have a flexibility which allows filling of the container so that it can be used as a pouch.

If the aqueous composition contains a preservative it is important that the concentration thereof is sufficient to maintain an antimicrobiological efficacy.

In a preferred embodiment, the container of this invention consists of a material which enables sterilization of the container in a convenient way, for example, by β or γ irradiation or by heating.

In a preferred embodiment, the container of this invention consists of a material which fulfills the following test for flexibility: Two rectangular pieces of the material being tested both having the size 60 mm×20 mm are welded together with a 3 mm welding zone forming a welded test pouch and, thereafter, 1.5 ml of water is filled into the pouch. If the overpressure is below 100 mBar, the material has a sufficient flexibility.

In a preferred embodiment of this invention, the container of this invention is to be used for storage of an aqueous pharmaceutical composition, optionally a solution or suspension of a pharmaceutically active compound.

In a preferred embodiment of this invention, the active ingredient in said pharmaceutical composition is a protein. In a further preferred embodiment of this invention, the active ingredient is insulin, growth hormone or factor VII and analogs thereof. In a preferred embodiment of this invention, the amount of insulin in the aqueous solution or suspension is in the range with the lower limit being about 10 U/ml, preferably about 40U/ml, more preferred about 100 U/ml, and even more preferred about 150 U/ml, and the upper limit being about 1500 U/ml, preferably about 1000 U/ml, more preferred about 500 U/ml, even more preferred about 300 U/ml.

In a preferred embodiment of this invention, the aqueous formulation contains a stabilizer. In a more preferred embodiment of this invention, the aqueous formulation contains phenol. In another preferred embodiment of this invention, the aqueous formulation contains m-cresol. In another preferred embodiment of this invention, the aqueous formulation contains benzyl alcohol. In a further preferred embodiment of this invention, the total concentration of phenol and/or m-cresol in the aqueous formulation is in the range from about 20 mM to about 50 mM, preferably in the range from about 30 mM to about 45 mM. The concentration of phenol and/or m-cresol is, inter alia, depending on the concentration of insulin in the aqueous formulation. In a preferred embodiment of this invention, the amount of phenol in the aqueous solution is in the range from about 15 to about 25 mM. In another preferred embodiment of this invention, the amount of m-cresol in the aqueous solution is in the range from about 15 to about 25 mM. In another preferred embodiment of this invention, the amount of benzyl alcohol in the aqueous formulation is in the range from about 15 to about 25 mM. In another preferred embodiment of this invention, there is no benzyl alcohol present in the aqueous formulation.

When electing the materials which are to be used for the preparation of the container of this invention, it is important to elect materials which do not absorb too much of the active ingredient and of the other ingredients present in the aqueous pharmaceutical composition.

As mentioned in the claims below, the container of this invention may be equipped with a device whereby said liquid can be expelled from said container (when desired). An example of such a device can be a septum for needle penetration in the form of a rubber material adhered on the inside or on the outside of the container foil or in the welding zone between the two foils. Another example can be an active or a passive closure valve adhered to the container. The container of this invention may be emptied by application of external pressure to the reservoir or by suction from a pump device.

The container of this invention can be used in many devices, for example, a pump, a syringe, or a pen like syringe. Conveniently, the container of this invention is disposable.

This invention also relates to a film material comprises at least two layers, said layers being joined intimately together, which film material can be used for preparing a transparent container according to this invention. In a preferred embodiment of this invention, the film material covered by this invention can be used directly to prepare the containers claimed herein. For example, the film material covered by this invention shall not be processed so that a further film is attached to the whole of one of the two surfaces.

The mentioning herein of references is no admission that they constitute prior art.

Herein, the word "comprise" is to be interpreted broadly meaning "include", "contain" or "comprehend" (vide Guidelines for Examination in the European Patent Office 2000, part C, chapter III, 4.13).

Test Methods

In a preferred embodiment, the container of this invention is prepared from pouch foils fulfilling some or all of the following tests:

Test A

Test for loss of m-cresol and pH change:

First, the foil is subjected to irradiation with 2×25 kGy e-beam on a number of planear A4 sheets having a total thickness less than 1 cm.

Thereafter, 10 cm$^2$ (2×5 cm$^2$) of the foil is cut into 15 minor parts sized (0.7×1 cm$^2$) and immersed into 1.5 ml of a solution containing about 1.80 mg/mL (19 mM) phenol, 2.06 mg/mL (19 mM) m-cresol, 16.0 mg/mL (174 mM) glycerol, 1.25 mg/mL (7 mM) disodium hydrogenphosphat, 0.58 mg/mL (10 mM) sodium chloride and pH: 7.40. The immersed sample and a reference sample are placed in an incubator at 37° C. for 1 week.

The content of m-cresol in the solution is analyzed by using a chromatographic method.

This test will show the total migration of m-cresol including the absorption directly into the adhesive at the edge. When stored at the above mentioned conditions, the following requirement should be fulfill: The maximum loss of m-cresol should be 10% and preferred less than 5%. The pH value of the solution should not change more than +/−0.2.

Test B

Test for permeation, loss of m-cresol and pH:

Paddington cup test method modified from DS/EN 13726-2.

In this method, a foil in test is placed between two flanges allowing 10 cm$^2$ of the inner foil (PE, PP or any other welding layer) to be in contact with 5 ml of a solution containing phenol: about 1.80 mg/mL (19 mM), m-cresol: 2.06 mg/mL (19 mM), glycerol: 16.0 mg/mL (174 mM), disodiumhydrogenphosphat: 1.25 mg/mL (7 mM), sodium chloride: 0.58 mg/mL (10 mM), and pH: 7.40. The Paddington cup is placed upside down allowing direct contact between the solution and the foil in an incubator at 37° C. and a relative humidity of max. 15% for 1 week along with a reference sample consisting of a Paddington cup with an inert aluminum foil. The Paddington cups are weighed before and after the storage. The content of m-cresol is analyzed by using a chromatographic method. This test is useful to test the total evaporation and will show the barrier properties against preservatives like m-cresol and phenol. When stored at the above mentioned conditions, the following requirement should be fulfilled: The maximum weight loss should be 2.5% preferred less than 1%, the maximum loss of m-cresol should be 10% and preferred less than 5%, and the pH value should not change more than +/−0.2.

Test C

Test of pouches with vehicle.

In this test, pouches are produced by welding the foil and by filling the pouches with vehicle. Some pouches are weighed before storage at 37° C. and a relative humidity of 15% and weighed after up till 12 weeks. Some pouches are stored at 37° C. and tested for content of m-cresol and phenol at regular intervals up to 12 weeks. Glass vials are used as a reference. When stored at the above mentioned conditions for 12 weeks, the following requirement should be fulfilled: The maximum weight loss shall be not more than 2.5%, preferred not more than 2%, the maximum loss of m-cresol shall be not more than 10% and preferred not more than 5%, the maximum loss of phenol shall be not more than 10% and preferred not more than 5%. The pH value should not change more than +/−0.2.

Test D

Transparency of a filled pouch.

A filled pouch must fulfill the transparency requirement in the European Pharmacopoeia 2001, $4^{th}$ Edition, part 3.2.2.1 concerning plastic containers for aqueous solutions for parenternal infusion. In this method, solution S is diluted 1:200 (for PE or PP) or 1:400 for other containers. This test can be modified by testing solution S diluted 1:50 or 1:100.

The following examples are offered by way of illustration, not by limitation.

EXAMPLE 1

50 micron of PCTFE is co-extruded with epoxy modified polyethylene imine (a tie-layer) and 50 micron of PE. This co-extruded foil is used for preparing the container containing approximately 1.5 ml by heat welding.

EXAMPLE 2

A co-extrude of PE-PET is laminated using a PU based adhesive to an laminate of Aclar® UltrRx2000 and PET giving a construction like PE-PET/Aclar®UltrRx2000/PET, where "/" indicates the use of an adhesive. This co-extruded foil is used for preparing the container containing approximately 1.5 ml by heat welding.

EXAMPLE 3

50 micron of PP is laminated on the PCTFE layer of the foil mentioned in example 1. The foil consisting of 3 polymers will be useful to produce pouches using the PE welding layer and which allow adhesion of a member consisting of a material allowing welding to the PP layer outside the pouch.

EXAMPLE 4

An experimental multilayer film consisting of 25 mµ PE and 50 mµ PCTFE (with a tie layer), made according to patent application Ser. No. PCT/BE03/000226 by Tekni-Plex Europe N.V., was tested under confidentiality agreement by tests A, B and C mentioned above. The results of these tests was as follows:

Test A: The loss of m-cresol was 1%. The pH value changed from 7.43 to 7.35.
Test B: The loss of m-cresol was 1%. The weight loss was 0.1%.
Test C: The weight loss was 1.3%. The loss of m-cresol was 8.7%. The loss of phenol was 2.1%. The pH value changed from 7.35 to 7.20 for drug product.

What is claimed is:

1. A flexible, at least partially transparent container for storage of a liquid pharmaceutical composition in a water-tight chamber, the container comprising:
   a liquid pharmaceutical composition comprising, an active ingredient and at least one preservative selected from the group consisting of phenol, m-cresol, and benzyl alcohol;
   a flexible wall material, that forms the water-tight chamber, comprising at least two layers, an inner layer consisting of polyethylene (PE) or polypropylene (PP) in intimate contact with said liquid pharmaceutical composition, and an outer layer consisting of polychlorotrifluoroethylene (PCTFE), said inner and outer layers being joined intimately together by a tie layer,
   wherein when said chamber is filled with water and stored at a temperature of about 5° C. for 24 months, less than 10% (weight/weight) of the content of water diffuses out from the container; and
   when said chamber is filled with water containing about 1.8 mg/mL (19 mM) of phenol and stored at a temperature of about 5° C. for 24 months, the change in the concentration of phenol in the liquid is less than about 10% (weight/weight),
   wherein the outer layer alone fulfills the requirement that when said chamber is filled with water and stored at a temperature of about 5° C. for 24 months less than 10% (weight/weight) of the content of water diffuses out from the container.

2. The container according to claim 1, wherein the outer layer alone fulfills the requirement that when said chamber is filled with water and when it is stored at a temperature of about 5° C. for 24 months less than 5% (weight/weight) of the content of water diffuses out from the container.

3. The container according to claim 1, wherein the inner layer is weldable.

4. The container according to claim 1, in which the thickness of the inner layer is between about 10 µm and about 60 µm.

5. The container according to claim 1 wherein the thickness of the tie layer is in the range from about 1 µm to about 10 µm.

6. The container according to claim 1, which container is equipped with a device whereby said liquid can be expelled from said container.

7. The container according to claim 1, wherein the liquid-tight chamber has a volume of at least about 0.5 ml and not more than about 10 ml.

8. The container according to claim 7 wherein the volume is from about 2 ml to about 4 ml.

9. A container according to claim 1, wherein at least 95% (volume/volume) of the water-tight chamber contains the liquid pharmaceutical composition.

10. The container according to claim 1, wherein the container is filled partially or wholly with the liquid pharmaceutical composition, and wherein the active ingredient is a peptide.

11. The container according to claim 10, wherein the peptide is insulin.

12. The container according to claim 11 wherein the content of insulin is in the range from about 10 U/ml to about 1500 U/ml.

13. A container according to claim 1 filled partially or wholly with a liquid pharmaceutical composition comprising phenol.

14. A container according to claim 1 filled partially or wholly with a liquid pharmaceutical composition comprising m-cresol.

15. A container according to claim 1 filled with a liquid pharmaceutical composition comprising benzyl alcohol.

16. A flexible, at least partially transparent container for storage of a liquid pharmaceutical composition in a water-tight chamber, the container comprising:
 a liquid pharmaceutical composition comprising, an active ingredient and at least one preservative selected from the group consisting of phenol, m-cresol, and benzyl alcohol; and
 a wall material that forms the water-tight chamber, comprising at least two layers, an inner layer consisting of a polyethylene (PE) or polypropylene (PP) film layer which is in intimate contact with said liquid pharmaceutical composition, and another layer consisting of a polychlorotrifluoroethylene (PCTFE) film layer, said two layers in direct contact by a tie layer, and either said inner layer and said PCTFE layer being a coextrudate or an extrusion-laminate, and the thickness of said PCTFE layer being between about 40 μm and about 100 μm.

17. The container according to claim 16, which is wholly transparent.

18. The container according to claim 16, wherein a third polymeric layer is added on the outer side of the PCTFE layer.

* * * * *

UNITED STATES PATENT AND TRADEMARK OFFICE
CERTIFICATE OF CORRECTION

| | | |
|---|---|---|
| PATENT NO. | : 8,399,078 B2 | Page 1 of 1 |
| APPLICATION NO. | : 11/283653 | |
| DATED | : March 19, 2013 | |
| INVENTOR(S) | : Madsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 967 days.

Signed and Sealed this

Second Day of December, 2014

Michelle K. Lee
*Deputy Director of the United States Patent and Trademark Office*